United States Patent
Berlin (10) Patent No.: US 7,179,594 B1
(45) Date of Patent: Feb. 20, 2007

(54) METHOD FOR DISTINGUISHING 5-POSITION METHYLATION CHANGES OF CYTOSINE BASES AND CYTOSINE-TO-THYMINE MUTATIONS AND FOR DETECTING SINGLE NUCLEOTIDE POLYMORPHISMS (SNPS) OR POINT MUTATIONS IN GENOMIC DNA

(75) Inventor: Kurt Berlin, Stahnsdorf (DE)

(73) Assignee: Epigenomics AG, Berlin (DE)

( * ) Notice: Subject to any disclaimer, the term of this patent is extended or adjusted under 35 U.S.C. 154(b) by 293 days.

(21) Appl. No.: 10/110,610

(22) PCT Filed: Oct. 13, 2000

(86) PCT No.: PCT/DE00/03726

§ 371 (c)(1),
(2), (4) Date: Oct. 21, 2002

(87) PCT Pub. No.: WO01/27317

PCT Pub. Date: Apr. 19, 2001

(30) Foreign Application Priority Data

Oct. 15, 1999 (DE) .................. 199 51 189

(51) Int. Cl.
C12Q 1/68 (2006.01)
C12P 19/34 (2006.01)
C07H 21/02 (2006.01)
C07H 21/04 (2006.01)

(52) U.S. Cl. .................. 435/6; 435/91.1; 435/91.2

(58) Field of Classification Search .................. 435/6, 435/91.1, 91.2, 287.2; 536/23.1, 24.3; 702/19, 702/20
See application file for complete search history.

(56) References Cited

U.S. PATENT DOCUMENTS 4,683,195 A * 7/1987 Mullis et al. .................. 435/6
6,214,556 B1 * 4/2001 Olek et al. .................... 435/6

FOREIGN PATENT DOCUMENTS

DE WO 99/28498 * 6/1999
WO WO 99/10540 * 3/1999

OTHER PUBLICATIONS

Kladde et al; Nucleic Acids Research, vol. 26, pp. 1354-1355, 1998.*

(Continued)

Primary Examiner—Jehanne Sitton
(74) Attorney, Agent, or Firm—Kriegsman & Kriegsman (57) ABSTRACT

A method is described for distinguishing 5-position methylation changes of cytosine bases and cytosine-to-thymine mutations and for the detection of single nucleotide polymorphisms (SNPs) or point mutations in genomic DNA, in which:

a) a genomic DNA sample is treated with sulfite or disulfite in such a way that all of the cytosine bases that are not methylated in the 5-position of the base are changed in such a way that a base is formed that is different in its base-pairing behavior, whereas the cytosines methylated at the 5-position remain unchanged, and b) an aliquot of the same genomic DNA sample is quantitatively methylated with Sss1 or another methyltransferase prior to the chemical treatment according to a) and c) both of the DNA samples treated in this way are investigated for the presence of cytosine by means of the same analytical method, and d) the cytosine positions that are determined are matched with a reference DNA sequence.

20 Claims, 1 Drawing Sheet

Comparative sequence
Unmethylated cytosine Methylated cytosine Mutation

Sequence 1

Sequence 1 after bisulfite treatment and amplification

Methylated Sequence 1

Methylated Sequence 1 after bisulfite treatment and amplification

OTHER PUBLICATIONS

Schumann et al; J. Mol. Biol. vol. 257, pp. 949-959, 1996.*
Chemical Abstracts Plus Accession No. 1996:85184 (Aral et al., Hum. Mutat., 7(1):52-8 (1996)), abstract only provided.
Chemical Abstracts Plus Accession No. 1998:734783 (El-Maarri et al., Am. J. Hum. Genet., 63(4):1001-8 (1998)), abstract only provided.
Chemical Abstracts Plus Accession No. 1997:40537 (Olek et al., Nucleic Acids Res., 24(24):5064-6 (1996)), abstract only provided.
Medline Abstracts Accession No. 96413032 (Paul et al., BIOTECHNIQUES, 21(1):126-33 (1996)), abstract only provided.
Biosis Abstracts Accession No. 1994:451668 (Kim et al., Cancer, 74(3):893-9 (1994)), abstract only provided.
Biosis Abstracts Accession No. 1996:526740 (Cravo et al., Gut, 39(3):434-8 (1996)), abstract only provided.
Biosis Abstracts Accession No. 1997:16178 (Gloria et al., Cancer, 78(11):2300-6 (1996)), abstract only provided.

* cited by examiner

Figure 1

```
                          SEQUENCE LISTING

<160> NUMBER OF SEQ ID NOS: 13

<210> SEQ ID NO 1
<211> LENGTH: 1085
<212> TYPE: DNA
<213> ORGANISM: Homo Sapiens

<400> SEQUENCE: 1
aaaagggtgg ggcttctatg gggggtcct  ctgtgtggcc gctgggcttg ggtattggga      60 agccggggt  atggcagggt gggcaagggg atggggtatt gacagttttg gaggtgatgc     120
cagccaggtt gggggcccac ctctgacctt gcttcacttc tgcagggcca ggatggtgct    180
aagggtgacc gaggcgagga tggtgagcca ggacagcctg tgagtgcctg gtgacccccac   240 cacccccctg agcccaagcc tcatcctctt taccoctctt ctgtgcccca ctcctgaggg    300
gtcccttggc tggaggataa acactcagcc acccaattc  ctctctccct agggatcccc    360
tggtcccacc ggggagaatg gaccccagg  gccacttgga aagcgagtaa gtgaggtgga    420
cccctgagac cttgggaggc agtccctggg ctgtgtgggg ggaggctggg caatggcagg    480
tgggatgggt ggggaggtgc ctggtgtctg cattgccctg ggtgtgtgtg tgtgcaggag    540
ctggtgggtt taagggygtg tggtatctca ttgcccgggg cagggtgtgt gtgcaggagc    600
tggtgggttt aagggtatgc ggtatctcat tgcactgggc gagtgtgtgt gcaggagctg    660
gtgggttgat gggtgtgcgg tatctcgggc atgtttgttc ctgggttctg gtgtgtatgt    720
tttcaccagg ggtagtggtg gttactgaca aagcagaatg gaaactggag gaggggctgg    780
ccagcttttc tgtgggccag gggtgaacct ttttagtttc tggggcagga gacgggccac    840
caggtagggt gtgggcaagt ggcccttcac caaatgtaca gactacccag tattttcaca    900
actgtcacag ctgtatctgt tctgcacatc tgtgaatcgg ccctcggcgc gtgtccctgt    960
gtatgcacgt gtgtgtgtgc atgtgtatgt gtgtgtctag gacaggaagg gggaagagtt   1020
gagcctggct gcccacggcc tcatgtgctc ttccttccca ctccacctgc agggtcctgc   1080
tggct                                                               1085

<210> SEQ ID NO 2
<211> LENGTH: 1085
<212> TYPE: DNA
<213> ORGANISM: Homo Sapiens

<400> SEQUENCE: 2
```

```
aaaagggtgg ggttttatg gggggtttt ttgtgtggtc gttgggtttg ggtattggga      60 agtcggggt atggtaggt gggtaagggg atgggtatt gatagttttg gaggtgatgt     120
tagttaggtt gggggtttat ttttgatttt gttttatttt tgtagggtta ggatggtgtt     180
aagggtgatc gaggcgagga tggtgagtta ggatagtttg tgagtgtttg gtgattttat     240 tattttttg agtttaagtt ttattttttt tattttttt ttgtgtttta tttttgaggg     300 gtttttggt tggaggataa atatttagtt attttaattt ttttttttt agggattttt     360 tggtttatc ggggagaatg gattttagg gttatttgga aagcgagtaa gtgaggtgga     420
tttttgagat tttgggaggt agttttggg ttgtgtggt ggaggttggg taatggtagg     480 tgggatggt ggggaggtgt ttggtgtttg tattgttttg ggtgtgtgtg tgtgtaggag     540
ttggtgggtt taagggygtg tggtattta ttgttcgggg tagggtgtgt gtgtaggagt     600
tggtgggttt aagggtatgc ggtatttat tgtattgggc gagtgtgtgt gtaggagttg     660
gtgggttgat gggtgtgcgg tatttcgggt atgtttgttt ttgggtttg gtgtgtatgt     720 ttttattagg ggtagtggtg gttattgata aagtagaatg gaaattggag gaggggttgg     780
ttagtttttt tgtgggttag gggtgaattt ttttagtttt tggggtagga gacgggttat     840
taggtagggt gtgggtaagt ggttttttat taaatgtata gattatttag tattttata     900 attgttatag ttgtatttgt tttgtatatt tgtgaatcgg ttttcggcgc gtgttttgt     960 gtatgtacgt gtgtgtgtgt atgtgtatgt gtgtgtttag gatagggaagg gggaagagtt    1020 gagtttggtt gtttacggtt ttatgtgttt ttttttttta ttttatttgt agggttttgt    1080
tggtt                                                                1085
```

<210> SEQ ID NO 3
<211> LENGTH: 1085
<212> TYPE: DNA
<213> ORGANISM: Homo Sapiens

<400> SEQUENCE: 3

```
aaaagggtgg ggttttatg gggggtttt ttgtgtggtt gttgggtttg ggtattggga      60
agttgggggt atggtaggt gggtaagggg atgggtatt gatagttttg gaggtgatgt     120
tagttaggtt gggggtttat ttttgatttt gttttatttt tgtagggtta ggatggtgtt     180
aagggtgatt gaggtgagga tggtgagtta ggatagtttg tgagtgtttg gtgattttat     240 tattttttg agtttaagtt ttattttttt tattttttt ttgtgtttta tttttgaggg     300 gtttttggt tggaggataa atatttagtt attttaattt ttttttttt agggattttt     360 tggtttatt ggggagaatg gattttagg gttatttgga aagtgagtaa gtgaggtgga     420
tttttgagat tttgggaggt agttttggg ttgtgtggt ggaggttggg taatggtagg     480 tgggatggt ggggaggtgt ttggtgtttg tattgttttg ggtgtgtgtg tgtgtaggag     540
ttggtgggtt taagggygtg tggtattta ttgtttgggg tagggtgtgt gtgtaggagt     600
tggtgggttt aagggtatgt ggtatttat tgtattgggt gagtgtgtgt gtaggagttg     660
gtgggttgat gggtgtgtgg tattttgggt atgtttgttt ttgggtttg gtgtgtatgt     720 ttttattagg ggtagtggtg gttattgata aagtagaatg gaaattggag gaggggttgg     780
ttagtttttt tgtgggttag gggtgaattt ttttagtttt tggggtagga gatgggttat     840
taggtagggt gtgggtaagt ggttttttat taaatgtata gattatttag tattttata     900 attgttatag ttgtatttgt tttgtatatt tgtgaattgg ttttggtgt gtgttttgt     960
```

-continued gtatgtatgt gtgtgtgtgt atgtgtatgt gtgtgtttag gataggaagg gggaagagtt    1020
gagtttggtt gtttatggtt ttatgtgttt tttttttta ttttatttgt agggttttgt    1080
tggtt    1085

<210> SEQ ID NO 4
<211> LENGTH: 19
<212> TYPE: DNA
<213> ORGANISM: Artificial Sequence
<220> FEATURE:
<223> OTHER INFORMATION: PRIMER 1 PRIMER FOR FRAGMENT 1

<400> SEQUENCE: 4
aaaagggtgg ggtttttat    19

<210> SEQ ID NO 5
<211> LENGTH: 20
<212> TYPE: DNA
<213> ORGANISM: Artificial Sequence
<220> FEATURE:
<223> OTHER INFORMATION: PRIMER 2 PRIMER FOR FRAGMENT 1

<400> SEQUENCE: 5
tctcctaccc caaaaactaa    20

<210> SEQ ID NO 6
<211> LENGTH: 21
<212> TYPE: DNA
<213> ORGANISM: Artificial Sequence
<220> FEATURE:
<223> OTHER INFORMATION: PRIMER 3 PRIMER FOR FRAGMENT 2

<400> SEQUENCE: 6
tttttggttg gaggataaat a    21

<210> SEQ ID NO 7
<211> LENGTH: 20
<212> TYPE: DNA
<213> ORGANISM: Artificial Sequence
<220> FEATURE:
<223> OTHER INFORMATION: PRIMER 4 PRIMER FOR FRAGMENT 2

<400> SEQUENCE: 7
aaccaacaaa accctacaaa    20

<210> SEQ ID NO 8
<211> LENGTH: 18
<212> TYPE: DNA
<213> ORGANISM: Artificial Sequence
<220> FEATURE:
<223> OTHER INFORMATION: OLIGONUCLEOTIDE 1 CG DINUCLEOTIDE

<400> SEQUENCE: 8
tttaagggcg tgtggtat    18

<210> SEQ ID NO 9
<211> LENGTH: 18
<212> TYPE: DNA
<213> ORGANISM: Artificial Sequence
<220> FEATURE:
<223> OTHER INFORMATION: OLIGONUCLEOTIDE 2 TG DINUCLEOTIDE

<400> SEQUENCE: 9
tttaagggtg tgtggtat    18

-continued

```
<210> SEQ ID NO 10
<211> LENGTH: 29
<212> TYPE: DNA
<213> ORGANISM: Homo Sapiens

<400> SEQUENCE: 10
ctggtgggtt taagggygtg tggtatctc                                    29

<210> SEQ ID NO 11
<211> LENGTH: 29
<212> TYPE: DNA
<213> ORGANISM: Artificial Sequence
<220> FEATURE:
<223> OTHER INFORMATION: CASE 1 UNMETHYLATED DNA BISULFITE TREATED
      METHYLATED C
      CASE 1 METHYLATED DNA BISULFITE TREATED METHYLATED C

<400> SEQUENCE: 11
ctggtgggtt taagggcgtg tggtatctc                                    29

<210> SEQ ID NO 12
<211> LENGTH: 29
<212> TYPE: DNA
<213> ORGANISM: Artificial Sequence
<220> FEATURE:
<223> OTHER INFORMATION: CASE 2 UNMETHYLATED DNA BISULFITE TREATED
      UNMETHYLATED C
      CASE 3 UNMETHYLATED DNA BISULFITE TREATED POINT MUTATION/SNP
      CASE 3 METHYLATED DNA BISULFITE TREATED POINT MUTATION/SNP

<400> SEQUENCE: 12
ttggtgggtt taagggtgtg tggtatttt                                    29

<210> SEQ ID NO 13
<211> LENGTH: 29
<212> TYPE: DNA
<213> ORGANISM: Artificial Sequence
<220> FEATURE:
<223> OTHER INFORMATION: CASE 2 METHYLATED DNA BISULFITE TREATED
      UNMETHYLATED C

<400> SEQUENCE: 13
ttggtgggtt taagggcgtg tggtatttt                                    29
```

METHOD FOR DISTINGUISHING 5-POSITION METHYLATION CHANGES OF CYTOSINE BASES AND CYTOSINE-TO-THYMINE MUTATIONS AND FOR DETECTING SINGLE NUCLEOTIDE POLYMORPHISMS (SNPS) OR POINT MUTATIONS IN GENOMIC DNA

The present invention concerns a method for distinguishing 5-position methylation changes of cytosine bases and cytosine-to-thymine mutations and for detecting single nucleotide polymorphisms (SNPS) or point mutations in genomic DNA.

The observational planes that have been well studied in molecular biology according to the method developments of the last few years include the genes themselves, the transcription of these genes into RNA and the translation of proteins that are formed therefrom. In the course of development of an individual, [the time] when and which gene is turned on and how the activation and inhibition of specific genes in specific cells and tissues is controlled can be correlated with high probability with the extent and nature of the methylation of the genes or of the genome. In this regard, the assumption is obvious that pathogenic conditions are expressed by a modified methylation pattern of individual genes or of the genome.

The present invention describes a method for the detection of the methylation state of genomic DNA samples, wherein mutations and cytosine methylations in particular can be distinguished from one another. The method may also be used for finding point mutations and single nucleotide polymorphisms (SNPs).

5-Methylcytosine is the most frequent covalently modified base in the DNA of eukaryotic cells. For example, it plays a role in the regulation of transcription, genomic imprinting and in tumorigenesis. The identification of 5-methylcytosine as a component of genetic information is thus of considerable interest. 5-Methylcytosine positions, however, cannot be identified by sequencing, since 5-methylcytosine has the same base pairing behavior as cytosine. In addition, in a PCR amplification, the epigenetic information which is carried by 5-methylcytosines is completely lost.

The modification of the genomic base cytosine to 5'-methylcytosine represents the epigenetic parameter that is most important up to the present time and has been best studied. Nevertheless, although today there are methods for determining complete genotypes of cells and individuals, there are still no comparable approaches for generating and evaluating epigenotypic information to such a great extent.

In principle, three methods that differ in principle are known for determining the 5-methyl status of a cytosine in the sequence context.

The principle of the first method is based on the use of restriction endonucleases (REs), which are "methylation-sensitive". REs are characterized by the fact that they introduce a cleavage in the DNA at a specific DNA sequence, for the most part between 4 and 8 bases long. The position of such cuts can then be detected by gel electrophoresis, [and then these segments are] transferred to a membrane and hybridized. Methylation-sensitive means that specific bases within the recognition sequence must be unmethylated, and thus the cleavage can be produced. The pattern of the bands after a restriction cleavage and gel electrophoresis thus changes, depending on the methylation pattern of the DNA. Of course, the least methylatable CpGs are found within the recognition sequences of REs and thus cannot be investigated according to this method.

The sensitivity of these methods is extremely low (Bird, A. P., and Southern, E. M., J. Mol. Biol. 118, 27–47). A variant combines PCR with these methods: an amplification by two primers lying on both sides of the recognition sequence is produced after a cleavage only if the recognition sequence is present in the methylated state. The sensitivity increases in this case to theoretically a single molecule of the target sequence, but of course, only individual positions can be investigated and with great expenditure (Shemer, R. et al., PNAS 93, 6371–6376). Also, it is assumed that the methylatable position is found within the recognition sequence of an RE.

The second variant is based on partial chemical cleavage of total DNA, according to the model of a Maxam-Gilbert sequencing reaction, ligation of adaptors to the thus-generated ends, amplification with generic primers and separation by gel electrophoresis. Defined regions up to a size of less than 1000 base pairs can be investigated by this method. The method, of course, is so complicated and unreliable that it is practically no longer used (Ward, C. et al., J. Biol. Chem. 265, 3030–3033).

A relatively new method which has been used most frequently in the meantime for investigating DNA for 5-methylcytosine is based on the specific reaction of bisulfite with cytosine, which is converted into uracil after subsequent alkaline hydrolysis, and uracil corresponds to thymidine in its base pairing behavior. 5-Methylcytosine, in contrast, is not modified under these conditions. Thus, the original DNA is converted in such a way that methylcytosine, which cannot originally be distinguished from cytosine by its hybridization behavior, now can be detected by "standard" molecular biological techniques as the single remaining cytosine, for example, by amplification and hybridization or sequencing. All of these techniques are based on base pairing, which can now be fully exploited. The state of the art, which concerns the sensitivity, is defined by a method which seals the DNA to be investigated in an agarose matrix, and in this way prevents the diffusion and renaturation of the DNA (bisulfite reacts only on single-stranded DNA) and replaces all precipitation and purification steps by rapid dialysis (Olek, A. et al., Nucl. Acids Res. 24, 5064–5066). Individual cells can be investigated with this method, which illustrates the potential of the method. Of course, previously, only individual regions of up to approximately 3000 base pairs long have been investigated; a global investigation of cells for thousands of possible methylation events is not possible. Of course, this method also cannot reliably analyze very small fragments from small quantities of sample. These are lost despite the protection against diffusion through the matrix.

An overview of the other known possibilities for detecting 5-methylcytosines can also be derived from the following review article: Rein, T., DePamphilis, M. L., Zorbas, H., Nucleic Acids Res. 26,2255 (1998).

With a few exceptions (e.g., Zeschnigk, M. et al., Eur. J. Hum. Gen. 5, 94–98; Kubota T. et al., Nat. Genet. 16, 16–17), the bisulfite technique has been previously applied only in research. But short, specific pieces of a known gene are always amplified after a bisulfite treatment and either completely sequenced (Olek, A. and Walter, J., Nat. Genet. 17, 275–276) or individual cytosine positions are detected by a "primer extension reaction" (Gonzalgo, M. L. and Jones, P. A., Nucl. Acids Res. 25, 2529–2531) or enzyme cleavage (Xiong, Z. and Laird, P. W., Nucl. Acids Res. 25, 2532–2534). In addition, detection by hybridizing has also been described (Olek et al., WO99 28498).

Other publications, which are concerned with the application of the bisulfite technique to methylation detection in the case of individual genes, are: Xiong, Z. and Laird, P. W. (1997), Nucl. Acids Res. 25, 2532; Gonzalgo, M. L. and Jones, P. A. (1997), Nucl. Acids Res. 25, 2529; Grigg, S. and Clark, S. (1994), Bioessays 16, 431; Zeschnik, M. et al. (1997), Human Molecular Genetics 6, 387; Teil, R. et al. (1994), Nucl. Acids Res. 22, 695; Martin, V. et al. (1995), Gene 157, 261; WO 97/46705, WO 95/15373 and WO 97/45560.

Commonalities between promoters exist not only in the presence of TATA or GC boxes, but also with respect to the transcription factors for which they possess binding sites and at what distance these sites are found relative to one another. The existing binding sites for a specific protein do not completely agree in their sequence, but conserved sequences of at least 4 bases are found, which may be elongated by the insertion of "wobbles", i.e., positions at which different bases are found each time. In addition, these binding sites are present at specific distances relative to one another.

A review of the state of the art in Oligomer Array Production may also be derived from a special publication of Nature Genetics that appeared in January 1999 (Nature Genetics Supplement, Volume 21, January 1999) and the references cited therein.

Matrix-assisted laser desorptions/ionization mass spectrometry (MALDI) is a new, very powerful development for the analysis of biomolecules (Karas, M. and Hillenkamp, F. 1998. Laser desorption ionization of proteins with molecular masses exceeding 10,000 daltons. Anal. Chem. 60: 2299–2301). An analyte molecule is embedded in a matrix absorbing in the UV. The matrix is evaporated in vacuum by a short laser pulse and the analyte is transported to the gas phase in an unfragmented state. An applied voltage accelerates the ions in a field-free flight tube. Ions are accelerated to varying degrees based on their different masses. Smaller ions reach the detector at an earlier time than the larger ions and the time of flight is converted into the mass of the ions.

Probes with several fluorescent labels have been used for scanning an immobilized DNA array. The simple introduction of Cy3 and Cy5 dyes to the 5'OH of the respective probe is particularly suitable for fluorescence labeling. The fluorescence of hybridized probes is detected, for example, by means of a confocal microscope. In addition to many others, the dyes Cy3 and Cy5 are commercially available.

Methylases, which methylate cytosine bases in specific sequence contexts are known and in part are also commercially available. Sss1 methylase, for example, methylates cytosine in the sequence context CpG (see e.g., Renbaum, P. et al. (1990), Nucleic Acids Res. 18, 1145) and can be obtained, e.g., from New England Biolabs, as well as other methylases such as Alu1, BamH1 or HaeIII.

Methylated cytosine positions cannot be reliably detected exclusively by bisulfite treatment, amplification and subsequent sequencing or hybridization, as is conducted in the state of the art. If a thymine is detected instead of a cytosine at the position in question, then this may involve a mutation in comparison to the considered reference sequence, but also may involve a non-methylated cytosine in the genomic sample DNA, which has been converted by the bisulfite treatment first to uracil and finally to thymine in the sequence context in the amplification. The object of the present invention is thus to solve this problem.

The object is solved by the fact that a method for distinguishing 5-position methylation changes of cytosine bases and cytosine-to-thymine mutations and for the detection of single nucleotide polymorphisms (SNPs) or point mutations in the genomic DNA is created, in which:

a) a genomic DNA sample is treated with sulfite or disulfite or another chemical in such a way that all of the cytosine bases not methylated at the 5-position of the base are changed in such a way that a base that differs in base pairing behavior is formed, while the cytosines methylated at the 5-position remain unchanged and b) an aliquot of the same genomic DNA sample is quantitatively methylated with Sss1 or another methyltransferase prior to the chemical treatment according to a), and c) both of the DNA samples thus treated are investigated for the presence of cytosine by means of the same analytical method and d) the determined cytosine positions are matched with a reference DNA sequence.

The present invention thus solves the object by the fact that a methylated aliquot of the same sample is uniformly treated and the sequence information obtained is matched with the sequence of a reference DNA, whereby a distinction is possible between mutations and cytosine methylation. In addition, it is also possible to find new mutations and polymorphisms, particularly C-T mutations, within the scope of this method.

A method is preferred according to the invention, wherein it is determined by means of the comparison of individual cytosine positions from the two differently treated samples with the reference sequence whether cytosine cannot be detected at a specific position and whether this is based on the fact that the cytosine is present in the genomic DNA in the unmethylated state or whether it is present, but changed by a mutation or a polymorphism, and thus is not present in the genomic DNA.

The invention is also a method, which is characterized by the fact that, prior to the detection of the cytosine bases, the two DNA samples or portions of these DNA samples are amplified by means of a cyclic process, namely the polymerase chain reaction or a comparable process.

It is preferred that more than 10 different fragments of the treated genomic DNAs are produced in one amplification batch.

It is also preferred that one uses for the amplification of the genomic DNA samples those primers, which contain so-called consensus sequences or such sequences important for gene regulation and which thus bind predominantly to regulating or coding sequences.

It is particularly preferred according to the invention that cytosine is detected in the specific context 5'-CpG-3'.

It is also preferred that one provides the DNA in the amplification with one or more detectable label(s) by incorporating nucleotide building blocks or oligonucleotides that are provided with a detectable label.

It is particularly preferred that the label is detected by fluorescence or chemiluminescence.

It is further preferred in the method according to the invention that cytosine is detected by means of hybridizing with oligomers specific for "sequence context-cytosine-sequence context", and these oligomers are attached in a defined arrangement on one or more surfaces.

It is preferred that for each cytosine to be detected in its sequence-specific context, at least one oligomer complementary to the sequence context is attached onto the surface, which [oligomer] contains the guanine complementary to the cytosine to be detected and another oligomer, which contains the base at the site of the cytosine to be detected which is complementary to the base to which unmethylated cytosines are converted by the chemical treatment.

In addition, it is preferred that for cytosine positions to be detected, those oligomers are attached, which bind specifically each time to the methylated and unmethylated position both to the plus strand as well as to the minus strand and/or specifically hybridize to the complementary strands that are formed by amplification.

It is also preferred that other oligomers are attached onto the surface, which bind each time to the sequence "sequence context-thymine-sequence context" and/or which detect cytosine and the base formed by chemical treatment in the plus strand, the minus strand and the strands arising each time by amplification of the complementary strands that form.

It is also preferred according to the invention that signals are detected from the oligomers at points on the surface(s) and these signals are specific for the methylated or unmethylated or mutated [positions] in the original genomic sample.

It is particularly preferred that the absolute degree of methylation and/or the homozygotic or heterozygotic status is determined by a comparison of the detected signals.

The invention also concerns the method, wherein the amplified fragments of the two samples are each attached onto a surface and sequence-specific oligomers provided with a detectable label are hybridized to these surfaces.

It is preferred that the analysis of hybridized sequence-specific oligomers is conducted by means of mass spectrometry and preferably with a MALDI mass spectrometer.

It is also preferred that the analysis of the hybridized sequence-specific oligomers is conducted by means of fluorescence or chemiluminescence.

A particularly preferred variant of the method according to the invention is that cytosine in the sequence context is detected by a polymerase reaction, which is specifically stopped when a cytosine base has been reached in the template, and the lengths of the fragments that are formed are measured.

It is particularly preferred, if the oligomers which are used for starting the primer-dependent polymerase reaction, a different sequence each time, are attached to different sites on a surface and the polymerase reaction is carried out on this surface.

It is also preferred that the oligomers that are utilized for starting the primer-dependant polymerase reaction are stripped from the surface by a chemical reaction or by light.

It is further preferred according to the invention that in order to terminate a polymerase reaction at the position of a cytosine or—in the counterstrand—a guanine, a nucleotide base is used, which also permits detection by means of a chemical modification, for example, by fluorescence, chemiluminescence or the binding of an antibody.

It is also preferred that the detection of the termination at the position of a cytosine or—in the counterstrand—a guanine is conducted by means of a length measurement of the fragments that have formed by gel electrophoresis, particularly capillary electrophoresis.

It is further preferred that the lengths of the fragments that have formed are measured by mass-spectrometric analysis and preferably in a MALDI mass spectrometer.

The method according to the invention is further characterized in that the reference DNA sequence originates from a database, namely from the human genome project.

Another subject of the present invention is a kit containing reference DNA and/or chemicals and other materials for conducting the bisulfite reaction and/or the amplification and/or a methyltransferase and/or documentation for conducting the method according to the invention.

Figure 1:
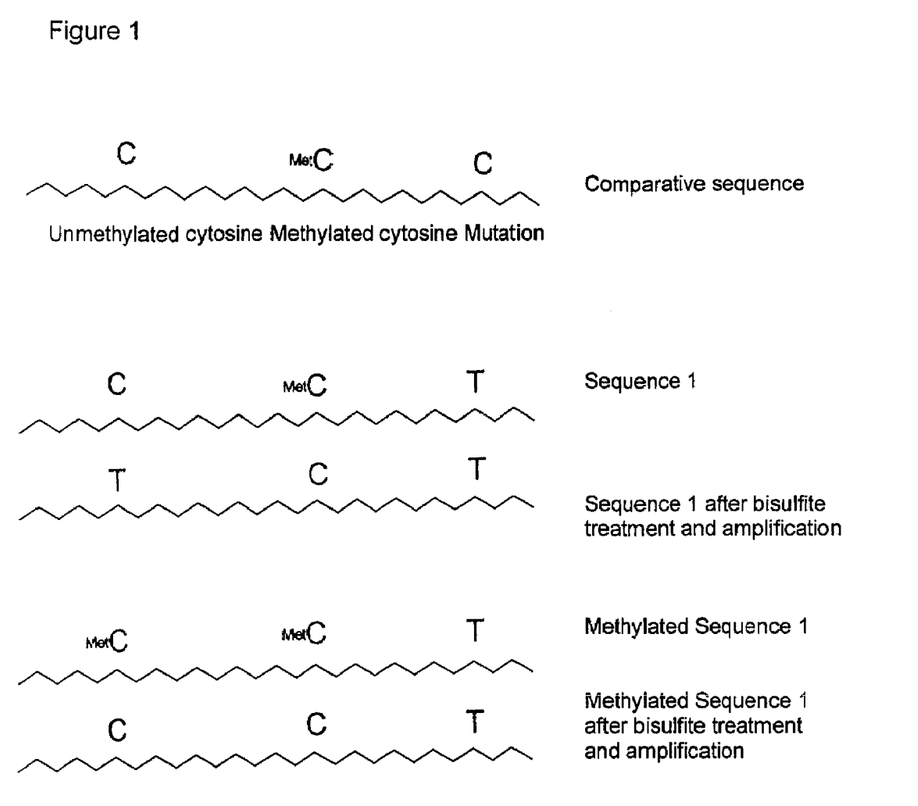

The described method serves for distinguishing 5-methylcytosine positions and point mutations/polymorphisms in genomic DNA, but may also be utilized for finding and for detecting point mutations/polymorphisms. FIG. 1 summarizes the method on the example of a random sequence 1.

The following steps are conducted for carrying out the method according to the invention:

A genomic DNA sample is chemically treated in such a way that all of the cytosine bases that are not methylated at the 5-position are changed in such a way that a base that is different in its base-pairing behavior is formed, while the cytosines that are methylated in the 5-position remain unchanged. Preferably, a treatment with a bisulfite solution (=hydrogen sulfite, disulfite) is conducted in this step, followed by alkaline hydrolysis. This treatment leads to a conversion of the unmethylated cytosine bases to uracil, whose base pairing behavior corresponds to thymine, [and these] respective positions are also present after the amplification.

In the second step, an aliquot of the same genomic DNA sample is methylated with Sss1 or another methyltransferase prior to the above-described chemical treatment. This methylation leads to the fact that all cytosine bases in the sequence context CG of the DNA sample or all cytosine bases of the DNA sample are converted to 5-methylcytosine with other methyltransferases, and thus a conversion to thymine can no longer occur with the chemical treatment. In a particularly preferred variant of the method, both DNA samples are amplified after the described pretreatment steps and this amplification is preferably carried out by means of PCR.

In a third step of the method, the two treated DNA samples are investigated for the presence of cytosine by means of the same analytical method. The determined cytosine positions are matched with those of a reference DNA sequence. This reference DNA sequence can be selected randomly in principle, but cannot be identical with the investigated sample. Preferably, the reference sequence originates from a database, such as formed currently, for example, within the scope of the human genome project or which already exists. The matching with the reference DNA may now lead to the following results, depending on the cytosine bases detected each time for a given position in the sample. If a cytosine is detected both in the methylated sample as well as in the unmethylated sample, then this cytosine is present in the methylated state in the genomic DNA. If a cytosine is detected only in the methylated sample and a thymine is detected in the unmethylated sample, then an unmethylated cytosine is present in the genomic DNA. In contrast, if a thymine is detected in both samples, but a cytosine is present in the reference sequence, then a C-T point mutation or a "single nucleotide polymorphism" (SNP) is present.

In a preferred variant of the method, the amplification is conducted in the second step, so that more than ten different fragments are produced in one amplification batch. This can be conducted preferably by using primers that contain so-called consensus sequences or such sequences important for gene regulation and which predominantly bind to regulating or coding sequences. With this amplification, the products are preferably provided with one or more detectable label(s), preferably by incorporation of nucleotide building blocks or oligonucleotides (e.g., primers) provided with a detectable label, whereby a detection of the label can be produced, most preferably by fluorescence or chemiluminescence.

The investigation of the cytosine positions is conducted in a particularly preferred variant of the method in such a way that cytosine is detected exclusively in the specific context 5'-CpG-3'. This may be conducted preferably by a detection of the cytosine by means of hybridizing with oligomers specific for "sequence context-cytosine-sequence context", [which] oligomers are attached in a defined arrangement on one or more surfaces. In a particularly preferred variant of the method, for each cytosine to be detected in its sequence-specific context, at least one oligomer which is complementary to the sequence context is attached onto the surface, which [oligomer] contains the guanine complementary to the cytosine to be detected, and another oligomer, which contains at the site of the cytosine to be detected the base which is complementary to the base in which unmethylated cytosine has been converted by chemical treatment. In a particularly preferred variant of the method, this involves here, if a bisulfite treatment is conducted, the base adenine which is complemetary to thymine.

In another particularly preferred variant of the method above, those oligomers, which bind specifically to the methylated and unmethylated cytosine positions both on the plus strand as well as on the minus strand or/and specifically hybridize to the complementary strands arising each time by amplification, are attached to the one or more surface(s) for the cytosine positions to be detected.

In another particularly preferred variant of the method, additional oligomers are attached onto the one or more surface(s), which bind specifically to the sequence, "sequence context-thymine-sequence context" and/or which detect cytosine and the base that is formed by chemical treatment in the plus strand, minus strand and the strands forming complementary strands that arise due to the amplification.

In a particularly preferred variant of the method, signals that are specific for the methylated or unmethylated or mutated [positions] in the original genomic sample are detected at the points of the surface(s), at which the oligomers are attached. In a preferred variant of the method, the detected signals can be quantified, so that the absolute degree of methylation and/or the homozygotic or heterozygotic status can be determined.

In another preferred variant of the method, the amplified fragments of the two samples, methylated and unmethylated, are attached to a surface, and sequence-specific oligomers provided with a detectable label are hybridized to both samples on this surface. In a particularly preferred variant of the method, the hybridized sequence-specific oligomers are detected by means of mass spectrometry and preferably with a MALDI mass spectrometer. In another, particularly preferred variant of the method, the analysis of the hybridized sequence-specific oligomer is conducted by means of its fluorescence or chemiluminescence.

In another preferred variant of the method, cytosine in the sequence context is detected by a polymerase reaction, which is stopped specifically when reaching a cytosine base in the template, and the lengths of the fragments that arise are measured. Oligomers, which are utilized for initiating the primer-dependant polymerase reaction, can be attached, preferably each different sequence to different sites on a surface and the polymerase reaction can be conducted preferably on this surface. In another particularly preferred variant of the method, the oligomers, which are utilized for initiating the primer-dependent polymerase reaction can be stripped off from the surface by a chemical reaction or by light. For termination of the polymerase reaction at the position of a cytosine or—in the counterstrand—of a guanine, a nucleaotide base is preferably used, which also permits detection by means of a chemical modification, for example, by fluorescence, chemiluminescence or the binding of an antibody. The detection of the termination at the position of a cytosine or—in the counterstrand—of a guanine may also be conducted by means of measuring the lengths of the fragments that are formed by gel electrophoresis, particularly capillary electrophoresis. In another preferred variant of the method, the lengths of the fragments that form are measured by mass-spectrometric analysis and preferably in a MALDI mass spectrometer.

For conducting the process, a kit can be used, which contains the reference DNA and/or chemicals and other materials for conducting the bisulfite reaction and/or the amplification and/or a methyltransferase and/or documentation for conducting the method.

The method according to the invention is explained on the basis of the appended figure.

In FIG. 1, point mutations of cytosine to thymine can be detected as thymine both in the bisulfite-treated and amplified DNA as well as in the bisulfite-treated and amplified DNA has that been methylated beforehand. Methylated cytosines are detected in both cases as cytosine, while in contrast, unmethylated cytosines are only detected in the unmethylated sample as T and in the methylated sample as C.

The following example explains the invention:

EXAMPLE

The following DNA sequence (SEQ ID NO: 1) will serve as an example, which contains a potential methylated CG dinucleotide or a point mutation CG to TG (C-SNP), the recitation of C/T is designated as a Y in the sequence listing:

Segment I) from the genomic sequence deposited in the database Genbank with the Accession Number AL031228 from position 117606 to position 118388.

I)

```
AAAAGGGTGGGGCTTCTATGGGGGGGTCCTCTGTGTGGCCGCTGGGCTTGGGTATTG

GGAAGCCGGGGGTATGGCAGGGTGGGCAAGGGGATGGGGTATTGACAGTTTTGGAGG

TGATGCCAGCCAGGTTGGGGGCCCACCTCTGACCTTGCTTCACTTCTGCAGGGCCAG

GATGGTGCTAAGGGTGACCGAGGCGAGGATGGTGAGCCAGGACAGCCTGTGAGTGCC

TGGTGACCCCACCACCCCCTGAGCCCAAGCCTCATCCTCTTTACCCCTCTTCTGTG

CCCCACTCCTGAGGGGTCCCTTGGCTGGAGGATAAACACTCAGCCACCCCAATTCCT

CTCTCCCTAGGGATCCCCTGGTCCCACCGGGGAGAATGGACCCCCAGGGCCACTTGG
```

-continued

AAAGCGAGTAAGTGAGGTGGACCCCTGAGACCTTGGGAGGCAGTCCCTGGGCTGTGT

GGGTGGAGGCTGGGCAATGGCAGGTGGGATGGGTGGGGAGGTGCCTGGTGTCTGCAT

TGCCCTGGGTGTGTGTGTGTGCAGGAGCTGGTGGGTTTAAGGGC/TGTGTGGTATCT

CATTGCCCGGGGCAGGGTGTGTGTGCAGGAGCTGGTGGGTTTAAGGGTATGCGGTAT

CTCATTGCACTGGGCGAGTGTGTGTGCAGGAGCTGGTGGGTTGATGGGTGTGCGGTA

TCTCGGGCATGTTTGTTCCTGGGTTCTGGTGTGTATGTTTTCACCAGGGGTAGTGGT

GGTTACTGACAAAGCAGAATGGAAACTGGAGGAGGGGCTGGCCAGCTTTTCTGTGGG

CCAGGGGTGAACCTTTTTAGTTTCTGGGGCAGGAGACGGGCCACCAGGTAGGGTGTG

GGCAAGTGGCCCTTCACCAAATGTACAGACTACCCAGTATTTTCACAACTGTCACAG

CTGTATCTGTTCTGCACATCTGTGAATCGGCCCTCGGCGCGTGTCCCTGTGTATGCA

CGTGTGTGTGTGCATGTGTATGTGTGTGTCTAGGACAGGAAGGGGGAAGAGTTGAGC

CTGGCTGCCCACGGCCTCATGTGCTCTTCCTTCCCACTCCACCTGCAGGGTCCTGCT

GGCT

The C/T in bold letters characterizes the C-SNP, which is found in the sequence with the Accession Number AL031228 at position 117606.

Sequence A) of the DNA that has been methylated and treated with bisulfite is shown below (SEQ ID NO:2).

A)

AAAAGGGTGGGGTTTTTATGGGGGGGTTTTTTGTGTGGTCGTTGGGTTTGGGTATTG

GGAAGTCGGGGGTATGGTAGGGTGGGTAAGGGGATGGGGTATTGATAGTTTTGGAGG

TGATGTTAGTTAGGTTGGGGGTTTATTTTTGATTTTGTTTTATTTTTGTAGGGTTAG

GATGGTGTTAAGGGTGATCGAGGCGAGCATGGTGAGTTAGGATAGTTTGTGAGTGTT

TGGTGATTTTATTATTTTTTGAGTTTAAGTTTTATTTTTTTATTTTTTTTTGTG

TTTTATTTTTGAGGGTTTTTTGGTTGGAGGATAAATATTTAGTTATTTTAATTTTT

TTTTTTTAGGGATTTTTTGGTTTTATCGGGGAGAATGGATTTTTAGGGTTATTTGG

AAAGCGAGTAAGTGAGGTGGATTTTTGAGATTTTGGGAGGTAGTTTTTGGGTTGTGT

GGGTGGAGGTTGGGTAATGGTAGGTGGGATGGGTGGGGAGGTGTTTGGTGTTTGTAT

TGTTTTGGGTGTGTGTGTGTGTAGGAGTTGGTGGGTTTAAGGGC/TGTGTGGTATTT

TATTGTTCGGGGTAGGGTGTGTGTGTAGGAGTTGGTGGGTTTAAGGGTATGCGGTAT

TTTATTGTATTGGGCGAGTGTGTGTGTAGGAGTTGGTGGGTTGATGGGTGTGCGGTA

TTTCGGGTATGTTTGTTTTGGGTTTTGGTGTGTATGTTTTTATTAGGGGTAGTGGT

GGTTATTGATAAAGTAGAATGGAAATTGGAGGAGGGGTTGGTTAGTTTTTTTGTGGG

TTAGGGGTGAATTTTTTAGTTTTTGGGGTAGGAGACGGGTTATTAGGTAGGGTGTG

GGTAAGTGGTTTTTTATTAAATGTATAGATTATTTAGTATTTTTATAATTGTTATAG

TTGTATTTGTTTTGTATATTTGTGAATCGGTTTTCGGCGCGTGTTTTTGTGTATGTA

CGTGTGTGTGTATGTGTATGTGTGTGTTTAGGATAGGAAGGGGGAAGAGTTGAGT

TTGGTTGTTTACGGTTTTATGTGTTTTTTTTTTTATTTTATTTGTAGGGTTTTGTT

GGTT

Sequence B) of the DNA that is not methylated and treated with bisulfite is shown below (SEQ ID NO:3).

B)

AAAAGGGTGGGGTTTTTATGGGGGGGTTTTTTGTGTGGTTGTTGGGTTTGGGTATTG
GGAAGTTGGGGGTATGGTAGGGTGGGTAAGGGGATGGGGTATTGATAGTTTTGGAGG
TGATGTTAGTTAGGTTGGGGGTTTATTTTTGATTTTGTTTTATTTTTGTAGGGTTAG
GATGGTGTTAAGGGTGATTGAGGTGAGGATGGTGAGTTAGGATAGTTTGTGAGTGTT
TGGTGATTTTATTATTTTTTGAGTTTAAGTTTTATTTTTTTATTTTTTTTTGTG
TTTTATTTTTGAGGGGT<u>TTTTTGGTTGGAGGATAAATA</u>TTTAGTTATTTTAATTTTT
TTTTTTTTAGGGATTTTTTGGTTTTATTGGGGAGAATGGATTTTTAGGGTTATTTGG
AAAGTGAGTAAGTGAGGTGGATTTTTGAGATTTTGGGAGGTAGTTTTTGGGTTGTGT
GGGTGGAGGTTGGGTAATGGTAGGTGGGATGGGTGGGGAGGTGTTTGGTGTTTGTAT
TGTTTTGGGTGTGTGTGTGTGTAGGAGTTGGTGGGTTTAAGGGC/TGTGTGGTATTT
TATTGTTTGGGGTAGGGTGTGTGTGTAGGAGTTGGTGGGTTTAAGGGTATGTGGTAT
TTTATTGTATTGGGTGAGTGTGTGTGTAGGAGTTGGTGGGTTGATGGGTGTGTGGTA
TTTTGGGTATGTTTGTTTTTGGGTTTTGGTGTGTATGTTTTTATTAGGGGTAGTGGT
GGTTATTGATAAAGTAGAATGGAAATTGGAGGAGGGGTTGGTTAGTTTTTTTGTGGG
TTAGGGGTGAATTTTTTTAGTTTTTGGGGTAGGAGATGGGTTATTAGGTAGGGTGTG
GGTAAGTGGTTTTTTATTAAATGTATAGATTATTTAGTATTTTTATAATTGTTATAG
TTGTATTTGTTTTGTATATTTGTGAATTGGTTTTTGGTGTGTGTTTTTGTGTATGTA
TGTGTGTGTGTATGTGTATGTGTGTGTTTAGGATAGGAAGGGGGAAGAGTTGAGT
TTGGTTGTTTATGGTTTTATGTGTTTTTTTTTTTATTTT<u>ATTTGTAGGGTTTTGTT</u>
<u>GGTT</u>

In the amplified fragment 1 with the length of 832 bp (positions 1 to 832), the C-SNP is found at position 557, while in the amplified fragment 2 with the length of 783 [bp] (positions 303 to 1085), the C-SNP is found at position 255. For fragment 1, the primers are shown in bold letters while for fragment 2 the primers are shown in bold letters and underlined.

Genomic DNA is cut with the restriction enzyme Mss1 (fermentase) and then methylated with the enzyme Sss1 (CpG methylase, BioLabs). The bisulfite reaction is conducted in a way known in and of itself. In the subsequent polymerase reaction, the gene COL11A2 is amplified on chromosome 6p21. The amplification is conducted according to the general PCR protocol with the pair of primers AAAAGGGTGGGGTTTTTAT (SEQ ID NO:4), TCTC-CTACCCCAAAAACTAA (SEQ ID NO:5) or with the pair of primers TTTTTGGTTGGAGGATAAATA (SEQ ID NO:6), AACCAACAAAACCCTACAAA (SEQ ID NO: 7). In this case, both primers or only one primer of the respective primer pairs was labeled with Cy5.

PCR batch (20 μL):
1 μL of DNA (10 ng), 2 μL of each dNTP (4×25 mM), 0.2 μL (1 unit) of Taq (Hot Star Taq®, Qiagen), 2 μL of PCR buffer (10×, Qiagen), 1 μL of each Cy5 labeled primer (6.25 pmol/μL). Two DNA fragments, which are represented in A) are amplified in this way.

Genomic DNA is cleaved with the restriction enzyme Mss1 (fermentase). The bisulfite reaction is conducted according to the indicated state of the art. In the subsequent polymerase reaction, the gene COL11A2 on chromosome 6p21 is amplified. The amplification is conducted according to the general PCR protocol with the pair of primers AAAAGGGTGGGGTTTTTAT (SEQ ID NO:4), TCTC-CTACCCCAAAAACTAA (SEQ ID NO:5) or with the pair of primers TTTTTGGTTGGAGGATAAATA (SEQ ID NO:6), AACCAACAAAACCCTACAAA (SEQ ID NO: 7). Both primers or only one primer of the respective pair of primers was labeled here with Cy5.

PCR Batch (20 μL):
1 μL of DNA (10 ng), 2 μL of each dNTP (4×25 mM), 0.2 μL (1 unit) of Taq (Hot Star Taq®, Qiagen), 2 μL of PCR buffer (10×, Qiagen), 1 μL of each Cy5 labeled primer (6.25 pmoL/μL). Two DNA fragments, which are represented in B, are amplified in this way.

For the analysis of the CG or TG dinucleotide shown in 1), the following oligonucleotides, which contain the sequences TTTAAGGGCGTGTGGTAT (SEQ ID NO:8) and TTTAAGGGTGTGTGGTAT (SEQ ID NO:9) were attached onto a glass surface. In separate experiments, glass slides with the DNA fragment 1 amplified from unmethylated, bisulfite-treated DNA and with the DNA fragment 1 amplified from methylated, bisulfite-treated DNA and/or with the DNA fragment 2 amplified from unmethylated bisulfite-treated DNA and with the DNA fragment 2 amplified from methylated bisulfite-treated DNA are used and hybridized in a way known in and of itself. This method is completely automated.

Proceeding from the genomic sequence CTGGTGGGTT-TAAGGGC/TGTGTGGTATCTC (SEQ ID NO:10), the following possible hybridizing results are conceivable, which make it possible to detect the methylation state or a point mutation in the CG dinucleotide:

Unmethylated DNA (bisulfite-treated)

Case 1) CTGGTGGGTTTAAGGGCGTGTGGTATCTC methylated C (SEQ ID NO: 11)

Case 2) TTGGTGGGTTTAAGGGTGTGTGGTATTTT unmethylated C (SEQ ID NO:12)

Case 3) TTGGTGGGTTTAAGGGTGTGTGGTATTTT point mutation/SNP (SEQ ID NO.12)

Methylated DNA (bisulfite-treated)

Case 1) CTGGTGGGTTTAAGGGCGTGTGGTATCTC methylated C (SEQ ID NO:11)

Case 2) TTGGTGGGTTTAAGGGCGTGTGGTATTTT unmethylated C (SEQ ID NO:13)

Case 3) TTGGTGGGTTTAAGGGTGTGTGGTATTTT point mutation/SNP (SEQ ID NO. 12)

Case 1: If a methylated cytosine is present in the genomic sequence, a cytosine is detected in the unmethylated bisulfite-treated DNA and in the methylated bisulfite-treated DNA.

Case 2: If an unmethylated cytosine is present in the genomic sequence, a thymine is detected in the unmethylated bisulfite-treated DNA and a cytosine is detected in the methylated bisulfite-treated DNA.

Case 3: If a point mutation (C-SNP) is present in the genomic sequence, a thymine is detected in the unmethylated bisulfite-treated DNA and in the methylated bisulfite-treated DNA.

What is claimed is:

1. A method for distinguishing between 5-position methylation changes of cytosine bases and cytosine-to-thymine mutations and detecting cytosine-to-thymine single nucleotide polymorphisms or point mutations, said method comprising the steps of:
   a) providing a first genomic DNA sample;
   b) providing a second genomic DNA sample, said first and second genomic DNA samples being identical to one another;
   c) treating said second genomic DNA sample, but not said first genomic DNA sample, with a methyltransferase, whereby all previously unmethylated cytosine bases in said second genomic DNA sample become methylated;
   d) chemically treating each of the first genomic DNA sample and the second genomic DNA sample treated with methyltransferase in step (c), with sulfite or bisulfite such that all of the unmethylated cytosine bases are changed whereas the methylated cytosine bases remain unchanged;
   e) determining the positions of cytosine in each of the first and second genomic DNA samples produced in step (d) using the same analytical method;
   f) comparing the cytosine positions of the first and second genomic DNA samples determined in step (e) to a reference DNA sequence and distinguishing 5-position methylation changes of cytosine bases and cytosine-to-thymine mutations; and
   g) detecting cytosine-to-thymine single nucleotide polymorphisms (SNPs) or point mutations in genomic DNA.

2. The method according to claim 1, further comprising, before said cytosine position determining step, the step of amplifying each of said chemically treated first and second genomic DNA samples or parts of said chemically treated first and second genomic DNA samples, said amplification being effected by a cyclical process prior to the detection of the cytosine base.

3. The method according to claim 2, further characterized in that more than 10 different fragments of the treated genomic DNA are produced in one amplification batch.

4. The method according to claim 1, further comprising, before said cytosine position determining step, the step of amplifying each of said chemically treated first and second genomic DNA samples, said amplifying step being effected using primers which contain consensus sequences for the first and second genomic DNA samples.

5. The method according to claim 1, wherein said cytosine position determining step comprises detecting cytosine in the specific context 5'-CpG-3'.

6. The method according to claim 1, further comprising, before said cytosine position determining step, the step of amplifying each of the first and second genomic DNA samples produced in step (d) using one or more detectable label(s) comprising nucleotide building blocks or oligonucleotides provided with a detectable label.

7. The method according to claim 6, wherein the detectable label is a fluorescent or chemilumenscent label.

8. The method according to claim 5, further characterized in that for each cytosine to be detected in its sequence-specific context, at least one oligomer which contains guanine and is complementary to the sequence context is attached to one or more surfaces and another oligomer which contains adenine at the site of the cytosine to be detected is attached to one or more surfaces.

9. The method according to claim 5, further characterized in that signals that are specific for methylated cytosines or unmethylated cytosines or cytosine-to-thymine mutations in the first genomic DNA sample are detected using oligomers attached to one or more surfaces.

10. The method according to claim 9, further characterized in that the absolute degree of methylation and/or the homozygotic or heterozygotic status is determined by a comparison of the detected signals.

11. The method according to claim 1, further characterized in that fragments of both the first and second genomic DNA samples produced in step (d) are amplified and attached onto a surface and hybridized with sequence-specific oligomers provided with a detectable label.

12. The method according to claim 11, further characterized in that the analysis of the hybridized sequence-specific oligomers is conducted with a MALDI mass spectrometer.

13. The method according to claim 11, further characterized in that the detectable label is a fluorescent or chemiluminescent label.

14. The method according to claim 1, wherein said cytosine position determining step comprises using a polymerase reaction, which is stopped specifically upon reaching a cytosine base in the template, and the lengths of the fragments that are formed are measured.

15. The method according to claim 14, wherein oligomers are utilized for initiating the polymerase reaction, and wherein each oligomer is fixed at a different site onto a surface and the polymerase reaction is conducted on this surface.

16. The method according to claim 14, wherein oligomers are utilized for initiating the polymerase reaction, said oligomers being stripped from the surface by a chemical reaction or by light.

17. The method according to claim 14, further characterized in that for the termination of the polymerase reaction at the position of a cytosine or—in a counterstrand—of a guanine, a nucleotide building block is used for detection via a chemical modification.

18. The method according to claim 14, further characterized in that the termination at the position of a cytosine or—in a counterstrand—of a guanine is detected by means of a length measurement of the fragments that arise by gel electrophoresis.

19. The method according to claim 14, further characterized in that the length measurement of the fragments that form is conducted by mass-spectrometric analysis.

20. The method according to one of the preceding claims, further characterized in that the reference DNA sequence originates from the human genome project.

* * * * *